United States Patent
Ströfer et al.

(10) Patent No.: US 6,610,888 B1
(45) Date of Patent: Aug. 26, 2003

(54) REACTION OF A SOLUTION COMPRISING A MIXTURE

(75) Inventors: Eckhard Ströfer, Mannheim (DE);
Stephan Scholl, Bad Dürkheim (DE);
Hans Hasse, Kaiserslautern (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/583,290

(22) Filed: May 31, 2000

(30) Foreign Application Priority Data

Jun. 7, 1999 (DE) .......................... 199 25 870

(51) Int. Cl.⁷ ........................ C07C 211/00; C07C 45/00; C07C 33/04; C07C 27/00; C07C 27/02; C07C 29/00; C07C 33/00; C07C 33/02; C07C 27/26; C07C 29/74

(52) U.S. Cl. ........................ 564/330; 564/331; 564/332; 564/333; 564/334; 568/457; 568/458; 568/467; 568/484; 568/873; 568/874; 568/876; 568/909.5; 568/913

(58) Field of Search .................. 564/330, 331, 564/332, 333, 334; 568/457, 458, 467, 484, 873, 874, 876, 909.5, 913

(56) References Cited

FOREIGN PATENT DOCUMENTS

DE    198 04 196 A1    8/1999

*Primary Examiner*—Samuel Barts
*Assistant Examiner*—Elvis O. Price
(74) *Attorney, Agent, or Firm*—Keil & Weinkauf

(57) ABSTRACT

A method of reacting a solution comprising a mixture of chemical compounds which are in chemical equilibrium with one another with at least one further chemical compound (9) is provided. The method comprises the following steps: fractionation of the solution by means of a separation method to give at least two fractions (5, 6) which are enriched in different chemical compounds of the mixture; and reaction of a fraction (5) with the further chemical compound or compounds (9). The fractionation is advantageously carried out using a film evaporator (1). Unreacted fractions (6) can be recirculated via a residence time vessel (3) back to the fractionation step. The method is particularly suitable for reactions of an aqueous formaldehyde solution in which various components of the solution (formaldehyde, methylene glycol, polyoxymethylene glycols) react in different ways.

25 Claims, 3 Drawing Sheets

REACTION OF A SOLUTION COMPRISING A MIXTURE

Figure 1:
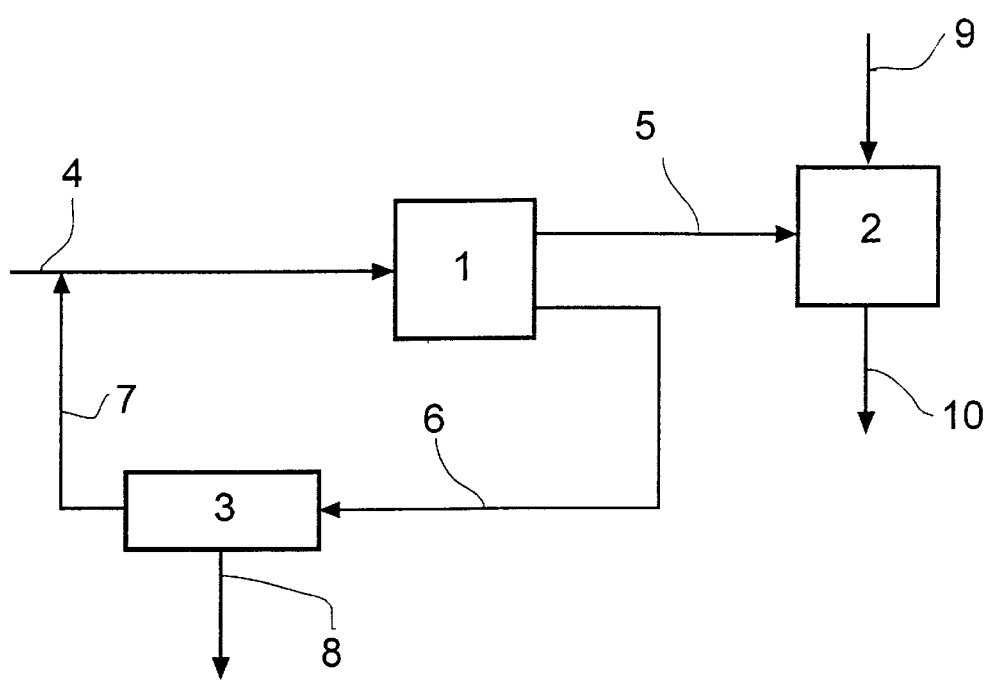

The present invention relates to a method of reacting a solution comprising a mixture of chemical compounds which are in chemical equilibrium with one another with at least one further chemical compound.

Chemically relevant substances in dissolved form are frequently present as a mixture of chemical compounds (components) which are in chemical equilibrium with one another. An industrially important example is aqueous solutions of formaldehyde. Formaldehyde is an important $C_1$ building block in the chemical industry; world production is about 12 million metric tons per year. Formaldehyde is one of the most reactive organic components and is sold in aqueous solution in concentrations of from 20 to 55%, and is used for many chemical reactions. An aqueous formaldehyde solution comprises an equilibrium mixture of formaldehyde, methylene glycol and oligomers made up of at least two methylene glycol units, namely polyoxymethylene glycols. All these constituents are interconverted at a finite rate depending on, for example, pH and temperature. Thus, for example, the polyoxymethylene glycols are degraded to methylene glycol at elevated temperature.

Chemical reactions in industrial reactors generally do not proceed with a selectivity of 100%. However, the selectivity to the desired main product can be controlled by clever management of the reaction conditions. In the case of syntheses using formaldehyde, such a control opportunity is provided by the form in which the aqueous formaldehyde solution is employed. Thus, the selectivity to the main product can be optimized by, for example, appropriate setting of the concentrations of formaldehyde, methylene glycol and higher polyoxymethylene glycols.

Such a setting of the concentrations has hitherto only been possible within a narrow window by means of appropriate selection of the pH, the dilution and the temperature. The same applies to many other solutions which comprise a mixture of chemical compounds which are in chemical equilibrium with one another.

It is an object of the present invention to provide a method of reacting such solutions, which method makes it possible to set the concentration of particular components of the mixture in a targeted way and thus to control the selectivity of the chemical reactions which occur.

Such a method is proposed in DE-A-198 04 196, which has earlier priority but is not a prior publication, for the reaction of a formaldehyde solution comprising polyoxymethylene glycols and possibly monomeric formaldehyde and/or methylene glycol with aniline in the presence of acid catalysts.

We have found that the object of the present invention is achieved by a method of reacting a solution comprising a mixture of at least two chemical compounds which are in chemical equilibrium with one another with at least one further chemical compound, which comprises the following steps:

a) fractionation of the solution by means of a separation method to give at least two fractions in which different chemical compounds of the mixture are present in increased concentrations compared to the chemical equilibrium; and b) reaction of one fraction with the further chemical compound or compounds before the chemical equilibrium is fully reestablished.

The use of a suitable separation method enables the concentrations of certain components of the mixture to be set in a targeted way within a very wide range. The concentrations of the components concerned are independent of parameters which can influence the course of the reaction in an undesirable manner, e.g. pH, dilution or temperature of the solution.

In order to ensure that the desired components in which the fraction has been enriched have not been reconverted into the other components which are in equilibrium with these components prior to the reaction, it is advantageous to make the time between the solution fractionation step and the reaction step shorter than the half-life time of the rate-determining step for establishment of the equilibrium between the components.

The separation method advantageously comprises at least the one step in which the solution is at least partly vaporized. The vaporization can advantageously be followed by an at least partial condensation.

The method of the present invention is particularly useful when the solution is a solution of an oligomer-forming substance in an appropriate solvent.

The method of the present invention can be particularly advantageously used when the solution is an aqueous formaldehyde solution comprising formaldehyde, methylene glycol and polyoxymethylene glycols made up of at least two methylene glycol units.

The fractions not employed in the reaction can, after appropriate further treatment, be once again treated by the method of the present invention. It is particularly advantageous for the equilibrium to be at least partially reestablished in at least one of the fractions not passed to the reaction by means of appropriate measures, e.g. a residence time apparatus, and for this fraction then to be returned to the separation step. In the simplest case, the residence time apparatus is a residence time vessel in which the fraction is left for a certain time.

To ensure uniform and favorable reaction conditions, it may be useful to remove solvent from the fraction introduced into the residence time apparatus. This can be done before or after this fraction passes through the residence time apparatus or while it is in the residence time apparatus.

For the fractionation step to give the different fractions, it is possible to use various separation methods. Particular advantages result from the fractionation being carried out using a thermal separation method in a film evaporator. Due to many control possibilities, various possible modes of operation and particular construction features, a film evaporator allows particularly precise setting of the concentrations of the components in the individual fractions. Furthermore, a film evaporator can be designed so that it can be scaled up or down without problems. Thus, the method of the invention can be used independently of scale in many applications.

Figure 2:
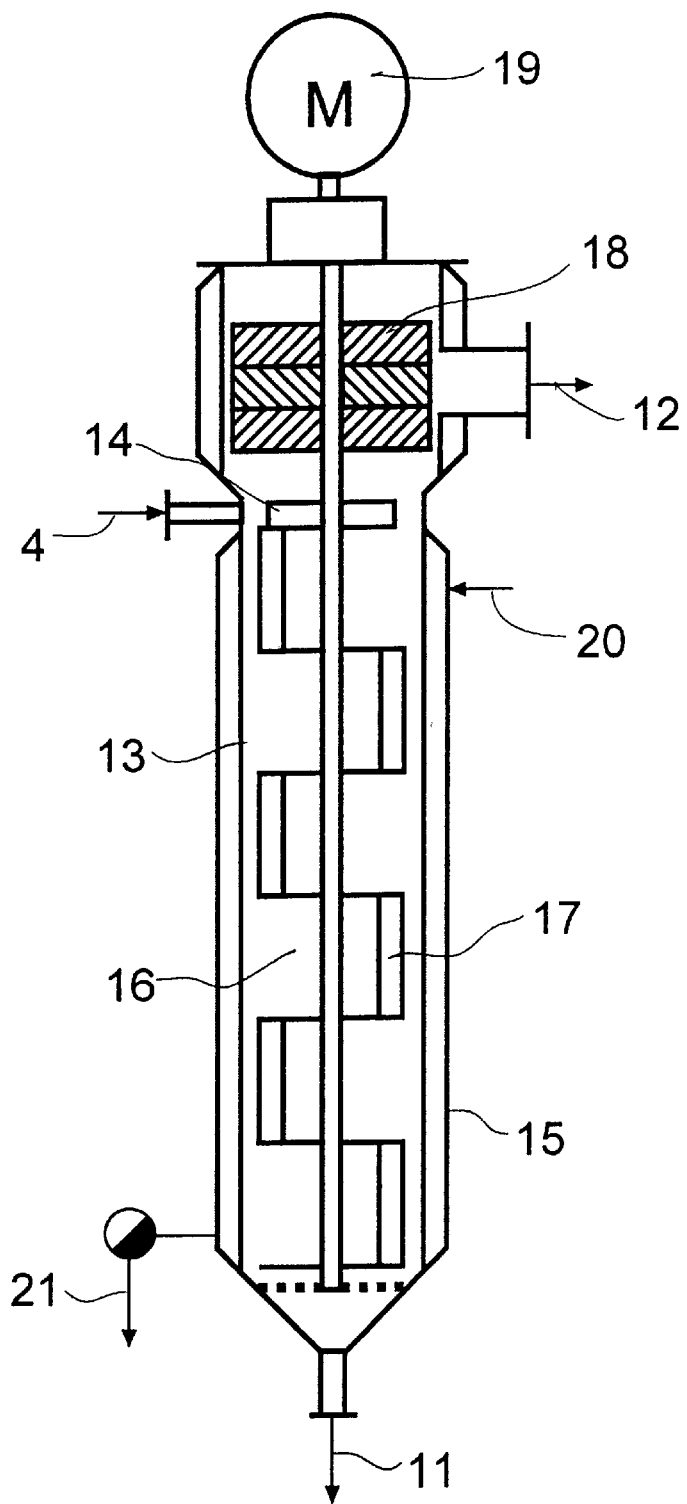
Figure 3:
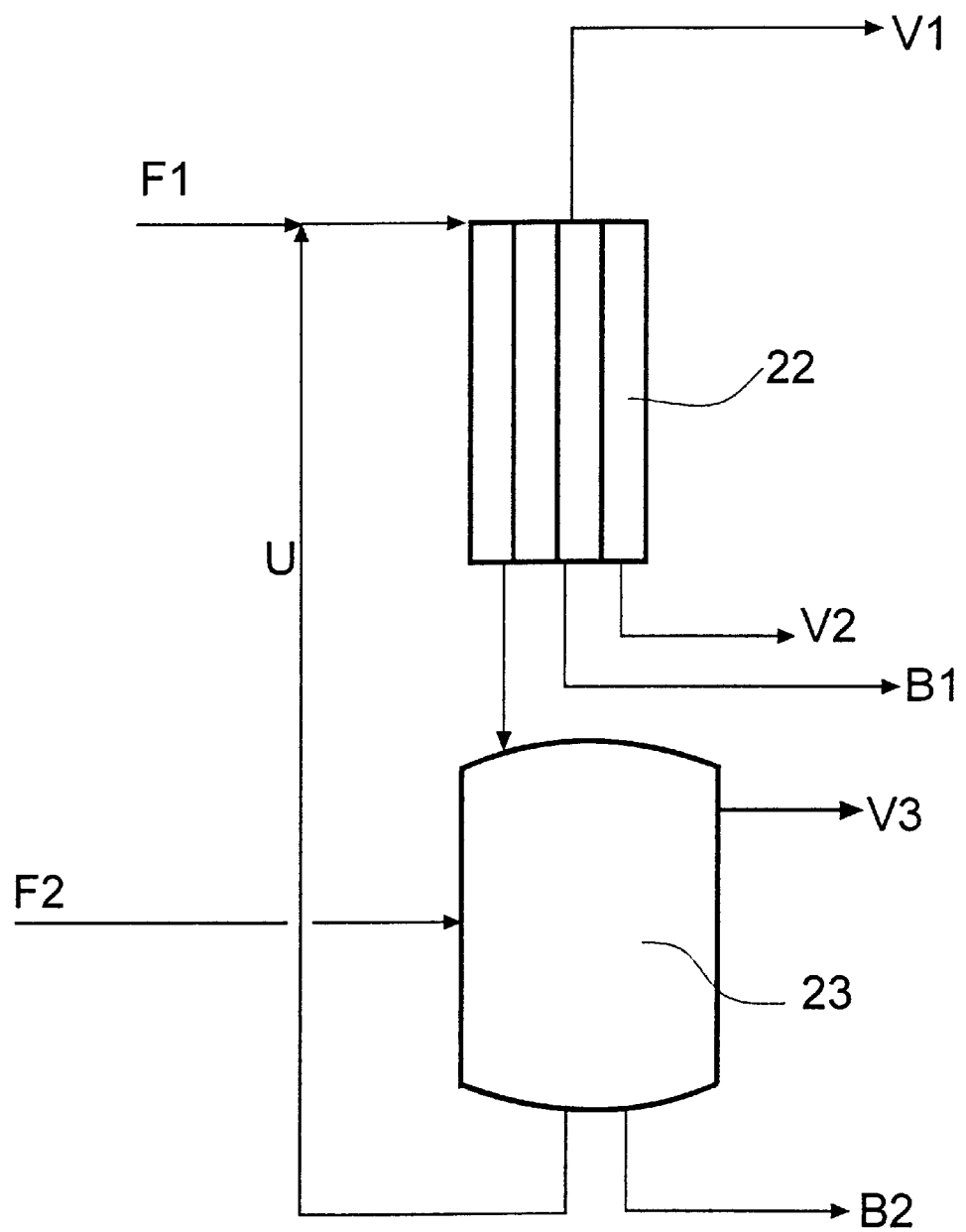

Particular embodiments of the present invention are described below with the aid of the attached drawings. In the drawings:

FIG. 1 shows a schematic flow diagram for the reaction of a solution comprising a mixture of chemical compounds which are in chemical equilibrium with one another using the method of the present invention, FIG. 2 schematically shows a possible embodiment of a film evaporator, and FIG. 3 gives an overview of various modes of operation for a film evaporator.

FIG. 1 schematically shows a flow diagram for, for example, reaction of an aqueous formaldehyde solution using the method of the present invention. A formaldehyde-containing crude solution 4, e.g. commercial 20–55% strength formaldehyde solution, is fed in via a feed line. This solution comprises a plurality of components which are in chemical equilibrium with one another. Formaldehyde (HCHO); methylene glycol ($CH_2(OH)_2$) formed from formaldehyde by reaction with water, and polyoxymethylene glycols ($HO(CH_2O)_nH$, $n \geq 2$), formed by condensation of the methylene glycol.

The crude solution 4 is fed to a film evaporator 1. In this, it is fractionated to give a desired fraction 5 and a residual fraction 6. The desired fraction 5 is enriched in, for example, polyoxymethylene glycols having a particular range of chain lengths n. The desired fraction is then fed to a main reactor system 2 where it is reacted with further starting materials 9 to form products 10.

The time interval between the time at which desired fraction 5 leaves the film evaporator and the time at which it is reacted in the main reactor system 2 is advantageously kept sufficiently short for the components of the formaldehyde solution (formaldehyde, methylene glycol and polyoxymethylene glycols) to be unable to undergo appreciable conversion into one another during this time interval. In particular, the time interval should be shorter than the half-life time of the rate-determining step for establishment of the equilibrium between the components of the solution under the given conditions. Thus, for example, at a temperature of 25° C., the time interval between leaving the film evaporator and the reaction should be less than 300–2500 s; at a temperature of 80° C., less than 2–10 s.

The residual fraction 6 is conveyed to a residence time vessel 3. The fraction remains in this for a time sufficient for the chemical equilibrium between formaldehyde, methylene glycol and the polyoxymethylene glycols to be at least partially reestablished. In practice, this time is from 5 to 20 minutes at temperatures from 50 to 100° C. At the same time, water is removed from the solution in the residence time vessel 3 by appropriate means (e.g. by distillation or extraction) in order to increase the concentration of the dissolved components. This is indicated by the water discharge stream 8. The removal of water can also be carried out before the undesired fraction is introduced into the residence time vessel 3 or after the solution leaves the residence time vessel 3. The resulting solution 7 is then mixed into the incoming crude solution 4 and once again introduced into the film evaporator 1.

A film evaporator which is particularly suitable for the method described is shown in FIG. 2. This is a thin film evaporator. The feed stream, consisting of crude solution 4 and possibly recirculation stream 7, is firstly fed to a liquid distributor 14. This distributes the crude solution over an evaporation surface 13. The evaporation surface 13 (heat transfer surface) usually has a cylindrical shape, but can also be at least partly conical. Depending on the application, it can be made of, for example, glass, stainless steel, enamel, graphite or a suitable plastic. It is in thermal contact with the inside of a heating jacket 15 which serves to supply heat to the evaporation surface 13. The liquid distributor 14 helps to distribute the feed solution uniformly over the circumference of the evaporation surface 13.

Rotating wiper blades 17 then distribute the solution further over the evaporation surface 13, serve to maintain and transport a liquid film on the evaporation surface 13 and help to intensify liquid-side heat and mass transfer. These wiper blades 17 are driven by a drive facility 19. Depending on the configuration and positioning of the wiping entity of the wiper blades 17, the liquid film can be either kept thin or be built up. This makes it possible to alter the residence time or the residence time distribution of the solution in the film evaporator. The typical residence time of the solution in the film evaporator is from 1 s to 10 minutes, preferably from 2 s to 2 minutes.

Through a heating medium inlet 20, a heating medium, e.g. steam, is fed into the heating jacket. This heats the evaporation surface. Cooled heating medium, e.g. condensed water in the case of steam as heating medium, is discharged via the heating medium outlet 21.

The heat supplied to the evaporation surface 13 vaporizes part of the solution fed to the film evaporator, as a result of which the composition of the unvaporized part of the solution changes. In addition, chemical reactions of the components of the mixture which are superposed on the evaporation process and lead to an increased yield of the desired component can occur in the evaporator. These reactions may also be dependent on the pH or/and on the concentration of the solvent. These parameters can be adjusted by addition of solvent, acid or alkali.

The resulting vapor (i.e. vaporized liquid or gases) enters a phase separation space 16 and from there goes to a droplet precipitator 18. Liquid droplets entrained in the vapor are removed from the gas phase here and are returned to the liquid (solution). The concentrate 11 is discharged in a suitable manner from the phase separation space 16. while the vapor 12 is taken off from the droplet precipitator 18. The vapor is introduced into a condenser which is not shown, where it is at least partly condensed to give a condensate.

When an aqueous formaldehyde solution is introduced into the film evaporator described, the polyoxymethylene glycols accumulate in the liquid 11 while the condensate from the vapor 12 is depleted in polyoxymethylene glycols and is rich in formaldehyde and methylene glycol. The result is two fractions, namely concentrate 11 and (part) condensate from the vapor 12, which have been selectively enriched in particular components of the crude solution 4 originally fed in.

Depending on the reaction to be carried out in the main reactor system 2, the desired fraction 5 in the flow diagram shown in FIG. 1 can be either the concentrate 11 or the (part) condensate. Accordingly, depending on the application, the other fraction in each case is passed to the residence time vessel 3.

In a particular embodiment, the condenser can be integrated into the body of the evaporator, which results in a shorter residence time of the vaporized components in the vapor phase and a more compact construction.

Suitable operating conditions for the film evaporator are generally a temperature of from 10° C. to 230° C., preferably from 10° C. to 150° C., at an absolute pressure of from 0.5 mbar to 2 bar. For the fractionation of an aqueous formaldehyde solution, preference is given to temperatures of from 20° C. to 100° C. at atmospheric pressure.

Apart from the embodiment of a film evaporator shown in FIG. 2, it is also possible to use an apparatus without mechanical influencing of the liquid film on the evaporation surface. The heat transfer surface of these falling film evaporators or falling stream evaporators can be configured as tubes or plates.

Depending on specific process requirements, a film evaporator can be used in various operating modes. FIG. 3 shows a schematic overview of the possible operating modes. Here, the actual film evaporator is designated by 20 and a vapor separator (i.e. phase separation space with droplet separator) is designated by 21. Both the film evaporator 20 and the vapor separator 21 can deviate from the specific construction shown in FIG. 2 and, compared to FIG.

2, have further inlets and outlets. V1, V2 and V3 designate gaseous streams, all other streams are usually liquid. Each of the streams V1, V2, V3, B1 and B2 taken off can be passed individually or after mixing (if appropriate after condensation) as desired fraction to the actual reaction in the main reactor system 2.

The film evaporator 22 can be operated so that the liquid feed passes through it once or so that the unvaporized liquid leaving it is circulated. In engineering terms, the circuit U is necessary for operation in the circulation mode. It can be either direct or via a residence time vessel. This circuit U is not to be confused with the recirculation 7 from FIG. 1 which can be independent of the operating mode of the film evaporator.

The following table indicates the active streams for the various possible operating modes.

|  | F1 | F2 | B1 | B2 | V1 | V2 | V3 | U |
|---|---|---|---|---|---|---|---|---|
| Single pass, vapor and liquid in countercurrent | X |  | X |  | X |  |  |  |
| Single pass, vapor and liquid in cocurrent | X |  | X |  |  | X |  |  |
| Circulation mode, feed into circuit, vapor and liquid in cocurrent | X |  |  | X |  | X |  | X |
| Circulation mode, feed into circuit, vapor and liquid in countercurrent | X |  |  | X | X |  |  | X |
| Circulation mode, feed into vapor separator, vapor and liquid in cocurrent |  | X | (X) | X |  | X | (X) | X |
| Circulation mode, feed into vapor separator, vapor and liquid in countercurrent |  | X |  | X | X |  | (X) | X |

In a variant of the method of the present invention, the film evaporator itself forms the main reactor 2 from FIG. 1. In this case, the reaction occurs in situ in the film evaporator after addition of at least one further starting material 9 at a suitable point on the film evaporator. This makes possible a very compact construction of the total reactor system and makes it possible to minimize the transfer time for the desired fraction between fractionation and reaction.

The use of a film evaporator, in particular the thin film evaporator shown in FIG. 2, for the fractionation of the crude solution 4 to give fractions 5 and 6 not only allows simple and reliable operation but also results in a series of further advantages. Thus, a film evaporator can be constructed in various sizes and for very different mass throughputs. A film evaporator can be operated either in conjunction with a mini reactor having a capacity of less than 0.5 kg/h or in combination with a macro reactor having a capacity of up to 30 metric tons/h. The method of the invention is thus extremely flexible and can be used for specialties in the pharmaceutical sector right through to large tonnage products. It can be scaled up and scaled down without problems both in respect of the achievable materials separation efficiency and in respect of the apparatus size required for a given production output.

Many applications are possible for the method described. The method can be used advantageously wherever the selectivity of a reaction depends on the concentration of a particular component of the crude solution compared to the concentrations of the other components.

The selectivity with which the main product is formed can be reduced by, for example, parallel reactions, with the rates of the main and secondary reactions having different temperature and concentration dependencies:

| HCHO, methylene glycol | +A → main product |
|---|---|
|  | +A → by-product |

If, for example, A is an amine which is to be methylated, it is kinetically advantageous for high concentrations of free HCHO and/or methylene glycol to be present from the beginning. In this case, the by-product is, for example, a condensation product. If the condensation product is the main product, it is advantageous to use higher polyoxymethylene glycols instead of HCHO and/or methylene glycol.

The selectivity can also be reduced by subsequent reactions of the main product:

| HCHO, methylene glycol | +A → main product |
|---|---|
| HCHO, methylene glycol | +main product → by-product |

Here, it is important to start with high HCHO or methylene glycol concentrations. Intermediates in the reaction of aldehydes with formaldehyde can, for example, be advantageously prepared in this way.

If the chemical reaction and a mixing process are superposed, it can likewise be important to set the concentrations of HCHO, methylene glycol and higher polyoxymethylene glycols so that the selectivity to the main product is optimized.

Examples of reactions for which the method of the invention can be used are given below:

Reaction of acetylene with aqueous formaldehyde solution in a Reppe reaction gives butynediol which is then hydrogenated to give butanediol. By means of Aldol reactions, formaldehyde is reacted with itself or higher aldehydes to form polyhydric alcohols such as sugars, pentaerythritol, trimethylolpropane and neopentyl glycol. Glycolic acid can be prepared from aqueous formaldehyde and CO. Chelating substances such as glycol nitriles are prepared from aqueous solutions of formaldehyde. In the Prins reaction, aqueous formaldehyde is reacted with olefins to give alpha-hydroxymethyl compounds.

Important condensation reactions are the reactions of aqueous formaldehyde with amines such as aniline or toluidine to give Schiff bases. Further reaction gives diphenylmethane derivatives such as methanediphenyldiamine. Formaldehyde reacts with hydroxylamine to give oximes. Aqueous formaldehyde and diols form cyclic ethers, for example dioxolane from glycol and formaldehyde.

This listing is not exhaustive. Textbooks on organic chemistry and industrial chemistry provide further examples of reactions. The listing is, however, intended to illustrate the industrial importance of formaldehyde as a synthetic building block in the overall area of organic chemistry. This applies both to small tonnage intermediates in the pharmaceutical or crop protection sectors, e.g. oximes, and to large tonnage products such as diphenylmethane derivatives.

The method described in detail here for aqueous formaldehyde solutions can also be advantageously used in a similar manner for other solutions which comprise a mixture of components which are in chemical equilibrium with one another. This applies particularly to solutions in which the dissolved material is a substance which forms oligomers. Examples of such solutions are:

solutions of alkyl thiols in sulfur, e.g. a methyl mercaptan (methyl thiol) solution which comprises dimethyl sulfide, dimethyl disulfide, dimethyl trisulfide, etc.

solutions of oligomer mixtures from condensation reactions.

LIST OF REFERENCE NUMERALS

1 Film evaporator
2 Main reactor system
3 Residence time vessel
4 Crude solution
5 Desired fraction
6 Undesired fraction
7 Recirculated solution
8 Discharge stream
9 Starting materials
10 Products
11 Concentrate
12 Vapor
13 Evaporation surface
14 Liquid distributor
15 Heating jacket
16 Phase separation space
17 Wiper blades
18 Droplet precipitator
19 Drive
20 Heating medium inlet
21 Heating medium outlet
22 Film evaporator
23 Vapor separator

We claim:

1. A method of increasing the concentration of one or more compounds in a solution comprising a mixture of at least two chemical compounds which are in chemical equilibrium with one another, with the exception of the reaction of a formaldehyde solution with aniline in the presence of acid catalysts, wherein the formaldehyde solution comprises polyoxymethylene glycols or polyoxymethylene glycols and monomeric formaldehyde or polyoxymethylene glycols and methylene glycol or polyoxymethylene glycols and monomeric formaldehyde and methylene glycol, which method comprises the following steps:

(a) fractionating the solution by means of a separation method to give at least two fractions in which different chemical compounds of the mixture are present in increased concentrations compared to the chemical equilibrium; and (b) reacting at least one of the compounds of increased concentration with a further chemical compound or compounds before the chemical equilibrium is fully reestablished in at least one of the fractions, and recovering the desired compound(s).

2. A method as claimed in claim 1, wherein the separation method comprises at least one step in which the solution is at least partly vaporized and the vaporization is preferably followed by an at least partial condensation.

3. A method as claimed in claim 1, wherein the solution is a solution of an oligomer-forming substance in a suitable solvent and the solution is preferably an aqueous formaldehyde solution comprising formaldehyde, methylene glycol and polyoxymethylene glycols.

4. A method as claimed in claim 1, wherein chemical equilibrium is at least partially reestablished in at least one of the fractions not passed to the reaction and this fraction is then once again fed to the separation step and the reestablishment of the chemical equilibrium preferably occurs in a residence time apparatus and the solvent is removed from the fraction fed to the residence time apparatus.

5. A method as claimed in claim 1, wherein a film evaporator is used for the fractionation.

6. A method as claimed in claim 2, wherein the vaporization is followed by an at least partial condensation.

7. A method as claimed in claim 3, wherein the solvent is capable of solving the oligomer-forming substance.

8. A method as claimed in claim 3, wherein the solution is an aqueous formaldehyde solution comprising formaldehyde, methylene glycol and polyoxymethylene glycols.

9. A method as claimed in claim 4, wherein the reestablishment of the chemical equilibrium occurs in a residence time apparatus.

10. A method as claimed in claim 9, wherein the solution is a solution of an oligomer-forming substance in a solvent and wherein the solvent is removed from the fraction fed to the residence time apparatus.

11. A method of increasing the concentration of one or more compounds in a solution comprising a mixture of at least two chemical compounds which are in chemical equilibrium with one another selected from the group consisting of aqueous formaldehyde solution, solutions of alkyl thiols in sulfur and solutions of oligomer mixtures, with the exception of the reaction of a formaldehyde solution with aniline in the presence of acid catalysts, wherein the formaldehyde solution comprises polyoxymethylene glycols or polyoxymethylene glycols and monomeric formaldehyde or polyoxymethylene glycols and methylene glycol or polyoxymethylene glycols and monomeric formaldehyde and methylene glycol, which method comprises the following steps:

(a) fractionating the solution by means of a separation method to give at least two fractions in which different chemical compounds of the mixture are present in increased concentrations compared to the chemical equilibrium; and (b) reacting at least one of the compounds of increased concentration with a further chemical compound or compounds before the chemical equilibrium is fully established in at least one of the fractions, and recovering the desired compound(s).

12. A method as claimed in claim 11, wherein said solution is an aqueous formaldehyde solution and said further chemical compound is selected from the group consisting of acetylene, formaldehyde, higher aldehydes, CO, olefins, amines such as aniline or toluidine, hydroxylamine and diols such as glycol forming butynediol resulting from aqueous formaldehyde solution and acetylene, polyhydric alcohols such as sugars, pentaerythritol, trimethylolpropane and neopentyl glycol from formaldehyde with formaldehyde or higher aldehydes, glycolic acid from aqueous formaldehyde and CO, alpha-hydroxymethyl from aqueous formaldehyde with olefins, schiff bases from aqueous formaldehyde with amines such as aniline or toluidine, oximes from formaldehyde with hydroxylamine and cyclic ethers from aqueous formaldehyde with diols such as dioxolane from glycol and formaldehyde.

13. A method as claimed in claim 11, wherein the separation method comprises at least one step in which the solution is at least partly vaporized.

14. A method as claimed in claim 11, wherein chemical equilibrium is at least partially reestablished in at least one of the fractions not passed to the reaction and this fraction is then once again fed to the separation step.

15. A method as claimed in claim 11, wherein a film evaporator is used for the fractionation.

16. A method as claimed in claim 13, wherein the vaporization is followed by an at least partial condensation.

17. A method as claimed in claim 11, wherein the solution is an aqueous formaldehyde solution comprising formaldehyde, methylene glycol and polyoxymethylene glycols.

18. A method as claimed in claim 11, wherein the reestablishment of the chemical equilibrium occurs in a residence time apparatus.

19. A method as claimed in claim 18, wherein the solution is a solution of an oligomer-forming substance in a solvent and wherein the solvent is removed from the fraction fed to the residence time apparatus.

20. A method of reacting an aqueous formaldehyde solution comprising a mixture of chemical compounds, including formaldehyde, methylene glycol and oligomers made up of at least two methylene glycol units, with at least one further chemical compound selected from the group consisting of acetylene, formaldehyde and higher aldehydes, CO, olefins, amines, hydroxylamine and diols, which method comprises the following steps:

(a) fractionation of said solution by means of a separation method to give at least two fractions in which fractions the chemical compounds of the mixture are present in increased concentrations compared to the chemical equilibrium, which said solution shows before this fractionation step and (b) reaction of one fraction with the further chemical compound or compounds before the chemical equilibrium is fully reestablished, with the exception of the reaction of a formaldehyde solution with aniline in the presence of acid catalysts, wherein the formaldehyde solution comprises polyoxymethylene glycols or polyoxymethylene glycols and monomeric formaldehyde or polyoxymethylene glycols and methylene glycol or polyoxymethylene glycols and monomeric formaldehyde and methylene glycol.

21. A method as claimed in claim 20, wherein the separation method comprises at least one step in which the solution is at least partly vaporized.

22. A method as claimed in claim 20, wherein chemical equilibrium is at least partially reestablished in at least one of the fractions not passed to the reaction and this fraction is then once again fed to the separation step.

23. A method as claimed in claim 20, wherein a film evaporator is used for the fractionation.

24. A method as claimed in claim 21, wherein the vaporization is followed by an at least partial condensation.

25. A method of increasing the concentration of one or more compounds in a solution comprising a mixture of water, formaldehyde, methylene glycol and oligomers made up of at least two methylene polymethylene glycols, which compounds are in chemical equilibrum, which method comprises the following steps:

(a) fractioning said solution by means of a separation method to give at least two fractions in which fractions the chemical compounds of the mixture are present in increased concentrations compared to the chemical equilibrium, and (b) reacting the compounds of increased concentration in at least one fraction with a further chemical compound or compound(s) before the chemical equilibrium is fully reestablished, and recovering the desired compound(s).

* * * * *

UNITED STATES PATENT AND TRADEMARK OFFICE
CERTIFICATE OF CORRECTION

PATENT NO.     : 6,610,888 B1
DATED          : August 26, 2003
INVENTOR(S)    : Stroefer et al.

It is certified that error appears in the above-identified patent and that said Letters Patent is hereby corrected as shown below:

Column 7,
Lines 51-52, delete "and the vaporization if preferably followed by an at least partial condensation";
Lines 54-57, "in a suitable solvent and the solution is preferably an aqueous formaldehyde solution comprising formaldehyde, methylene glycol and polyoxymethylene glycols" should be -- in a solvent --.
Lines 61-65, delete "and the reestablishment of the chemical equilibrium preferably occurs in a residence time apparatus and the solvent is removed from the fraction fed to the residence time apparatus".

Column 8,
Line 4, "solving" should be -- dissolving --.

Signed and Sealed this

Sixteenth Day of December, 2003

JAMES E. ROGAN
*Director of the United States Patent and Trademark Office*